US009243061B2

(12) United States Patent
Hamilton et al.

(10) Patent No.: US 9,243,061 B2
(45) Date of Patent: *Jan. 26, 2016

(54) OSTEOARTHRITIS TREATMENT

(75) Inventors: John Allan Hamilton, Carlton (AU); Andrew David Cook, Carlton (AU)

(73) Assignee: University of Melbourne (AU)

( * ) Notice: Subject to any disclaimer, the term of this patent is extended or adjusted under 35 U.S.C. 154(b) by 0 days.

This patent is subject to a terminal disclaimer.

(21) Appl. No.: 13/140,467

(22) PCT Filed: Dec. 21, 2009

(86) PCT No.: PCT/AU2009/001672
§ 371 (c)(1),
(2), (4) Date: Aug. 4, 2011

(87) PCT Pub. No.: WO2010/071924
PCT Pub. Date: Jul. 1, 2010

(65) Prior Publication Data
US 2012/0003234 A1 Jan. 5, 2012

Related U.S. Application Data

(60) Provisional application No. 61/139,679, filed on Dec. 22, 2008, provisional application No. 61/164,486, filed on Mar. 30, 2009.

(51) Int. Cl.
*C07K 16/24* (2006.01)
*A61K 39/395* (2006.01)
*A61K 39/00* (2006.01)

(52) U.S. Cl.
CPC ............ *C07K 16/243* (2013.01); *A61K 39/395* (2013.01); *A61K 2039/505* (2013.01); *C07K 2317/76* (2013.01)

(58) Field of Classification Search
None
See application file for complete search history.

(56) References Cited

U.S. PATENT DOCUMENTS

| 5,475,087 | A | 12/1995 | Seelig |
| 5,747,032 | A | 5/1998 | Metcalf et al. |
| 5,932,704 | A | 8/1999 | Jubinsky |
| 6,300,064 | B1 | 10/2001 | Knappik et al. |
| 7,427,401 | B2 | 9/2008 | Lopez et al. |
| 7,455,836 | B2 | 11/2008 | Hamilton et al. |
| 7,741,450 | B2 * | 6/2010 | Sass et al. ............ 530/388.23 |
| 7,867,495 | B2 * | 1/2011 | Steidl et al. ............ 424/141.1 |
| 7,935,795 | B2 | 5/2011 | Nakajima |
| 2002/0010126 | A1 | 1/2002 | Hamilton et al. |
| 2002/0141994 | A1 | 10/2002 | Devalaraja et al. |
| 2004/0241755 | A1 * | 12/2004 | Buckbinder et al. ........ 435/7.2 |
| 2006/0067938 | A1 * | 3/2006 | Daouti et al. ............ 424/146.1 |
| 2007/0197434 | A1 * | 8/2007 | Nakao et al. .................. 514/12 |
| 2007/0243225 | A1 | 10/2007 | McKay |
| 2008/0227789 | A1 * | 9/2008 | Goff et al. .................... 514/249 |
| 2008/0292641 | A1 * | 11/2008 | Sass et al. .................... 424/172.1 |
| 2008/0311111 | A1 * | 12/2008 | Drew et al. .................. 424/130.1 |
| 2009/0163440 | A1 * | 6/2009 | Waddell et al. ................ 514/54 |

FOREIGN PATENT DOCUMENTS

| WO | 9102063 | 2/1991 |
| WO | 9409149 | 4/1994 |
| WO | 03068920 | 8/2003 |
| WO | 2005105844 | 11/2005 |
| WO | 06023412 | 3/2006 |
| WO | 2006111353 | 10/2006 |
| WO | 2006122797 | 11/2006 |
| WO | WO 2006/122797 A2 * | 11/2006 |
| WO | 2007092939 | 8/2007 |
| WO | 2007110631 | 10/2007 |
| WO | 2008/064321 | 5/2008 |
| WO | 2008141391 | 11/2008 |
| WO | 2009038760 | 3/2009 |
| WO | 2009062238 | 5/2009 |
| WO | 2009064399 | 5/2009 |
| WO | 2009134805 | 11/2009 |
| WO | AU2009/001672 | 7/2010 |
| WO | 2010124163 | 10/2010 |

OTHER PUBLICATIONS

U.S. Appl. No. 13/903,009, filed May 28, 2013.*
Kato et al. Neoantigens in osteoarthritic cartilage. Curr Opin Rheumatol. Sep 2004;16(5):604-8.*
Campbell et al., 'Collagen-induced arthritis in C57BL/6 (H-2) mice: new insights into an important disease model of rheumatoid arthritis,' Eur. J. Immunol., 2000, 30:1568-1575.
Campbell, I.K. et al., The colony-stimulating factors and collagen-induced arthritis: exacerbation of disease by M-CSF and G-CSF and requirement for endogenous M-CSF, Journal of Leukocyte Biology, vol. 68, Jul. 2000, 144-150.
Firestein, G.S. et al., Cytokines in Chronic Inflammatory Arthritis, The Rockefeller University Press vol. 168, Nov. 1988, 1573-1586.
Hazenberg et al., 'Correction of granulocytopeani in Felty's Syndrome by granulocyte-macrophage colony-stimulating factor. Simultaneous induction of interleukin-6 release and flare-up of the arthritis,' Blood, Dec. 1989, 74(8):2769-2770 (correction to previous citation as p. 2769-2780).
Hercus et al., 'Specific human granulocyte-macrophage colony-stimulating factor antagonists,' PNAS, Jun. 1994, 91:5838-5842.

(Continued)

*Primary Examiner* — David Romeo
(74) *Attorney, Agent, or Firm* — Ropes & Gray LLP

(57) ABSTRACT

The present invention relates generally to a method for the treatment and/or prophylaxis of osteoarthritis (OA). In accordance with the present invention, an antagonist of GM-CSF can be effective in the treatment of osteoarthritis. An antagonist of GM-CSF includes, but is not limited to, an antibody that is specific for GM-CSF or the GM-CSF receptor. The present invention further provides transgenic animals, such as a GM-CSF knock-out mouse, useful for testing antagonists in certain disease models.

1 Claim, 6 Drawing Sheets

(56) References Cited

OTHER PUBLICATIONS

Kinne et al., 'Macrophages in rheumatoid arthritis,' Arthritis Research, 2000, 2 (3):189-202.
Leizer et al., 'Cytokine Regulation of Colony-Stimulating Factor Production in Cultured Human Synovial Fibroblasts: I. Induction of GM-CSF and G-CSF Production by Interleukin-1 and Tumor Necrosis Factor,' Blood, Nov. 15, 1990, 76(10):1989-1996.
Metcalf, Donald, 'The Florey Lecture, 1991: The Colony-Stimulating Factors: Discovery to Clinical Use,' Philosophical Transactions: Biological Sciences, Jul. 29, 1991, 333(1266):147-173.
Williamson et al., "The detection and initial characterization of colony-stimulating factors in synovial fluid," Clin. Exp. Immunol., 1988, 72:67-73.
Alvaro-Gracia et al., "Cytokines in chronic inflammatory arthritis. VI. Analysis of the synovial cells involved in granulocyte-macrophage colony-stimulating factor production and gene expression in rheumatoid arthritis and its regulation by IL-1 and tumor necrosis factor-a," J Immunol., May 15, 1991, 146(10):33653371.
Burmester et al., "Mononuclear phagocytes and rheumatoid synovitis. Mastermind or workhorse in arthritis?" Arthritis & Rheumatism, Jan. 1997, 40(1)5-18.
Campbell et al., "Granulocyte-macrophage colony stimulating factor exacerbates collagen induced arthritis in mice," Ann. Rheum. Dis., 1997, 56:364-368.
Campbell et al., "Protection from collagen-induced arthritis in granulocyte-macrophage colony-stimulating factor-deficient mice," J. Immunol., 1998, 161:3639-3644.
Cook et al., "Blockade of collagen-induced arthritis post-onset by antibody to granulocyte-macrophage colony-stimulating factor (GM-CSF): requirement for GM-CSF in the effector phase of disease," Arthritis Research, 2001, 3:293-298.
de Vries et al., "Flare-up of rheumatoid arthritis during GM-CSF treatment after chemotherapy," Lancet, Aug. 24, 1991, 338:517-518.
Hamilton,J.A., "Rheumatoid arthritis: opposing actions of hemopoietic growth factors and slow acting anti-rheumatic drugs," Lancet, Aug. 28, 1993, 342:536-539.
Hamilton,J.A., "GM-CSF in inflammation and autoimmunity," Trends Immunol., Aug. 2002, 23(8):403408.
Haworth et al., "Expression of granulocyte-macrophage colony-stimulating factor in rheumatoid arthritis: regulation by tumor necrosis factor-a," Eur. J. Immunol., 1991, 21:2575-2579.
Kastelein et al., "GM-CSF receptor: interactions and activation," Oncogene, 1993, 8:231-236.

Krinner et al., "A human monoclonal IgG1 potently neutralizing the pro-inflammatory cytokine GM-CSF," Molecular Immunology, Feb. 2007, 44 (5):916-925.
McQualter et al., "Granulocyte macrophage colony-stimulating factor: a new putative therapeutic target in multiple sclerosis," J. Exp. Med., Oct. 1, 2001, 194(7):873-881.
Meager et al., "Spontaneously occurring neutralizing antibodies against granulocyte-macrophage colony-stimulating factor in patients with autoimmune disease," Immunology, 1999, 97:526-532.
Mulherin et al., "Synovial tissue macrophage populations and articular damage in rheumatoid arthritis.," Arthritis & Rheumatism, Jan. 1996, 39(1):115-124.
Olver et al., "A phase I study of the GM-CSF antagonist E21R," Cancer Chemother. Pharmacol., 2002, 50:171-178.
Santiago-Schwarz et al., "Dendritic cells (DCs) in rheumatoid arthritis (RA): progenitor cells and soluble factors contained in RA synovial fluid yield a subset of myeloid DCs that preferentially activate Th1 inflammatory-type responses," J. Immunol., 2001, 167:1758-1768.
Xu et al., "Cytokines in chronic inflammatory arthritis. II. Granulocyte-macrophage colony-stimulating factor in rheumatoid synovial effusions," J. Olin. Invest., Mar. 1989, 83:876-882.
Plater-Zyberk C. et al. GM-CSF Neutralisation Suppresses Inflammation and Protects Cartilage in Acute Streptococcal Cell Wall Arthritis of Mice // Ann Rheum Dis. Apr. 2007; 66(4); 452-457. Published online Oct. 4, 2006. doi: 10.1136/ard.2006.057182 PMCID: PMC1856054.
PCT/AU2009/001672 International Preliminary Report on Patentability dated Feb. 2, 2010.
PCT/AU2009/001672 International Search Report dated Feb. 13, 2010.
Grunke M. et al. Successful Treatment of Inflammatory Knee Osteoarthritis with Tumor Necrosis Factor Blockade // Ann Rheum Dis., Apr. 2006; 65(4): 555-556, doi: 10.1136/ard.2006.053272.
Amos et al.: "Adenoviral gene transfer into osteoarthritis synovial cells using the endogenous inhibitor IkBβ reveals that most, but not all , inflammatory and destructive mediators are NFKB dependent" Rheumatology 2006;0:1201-1209.
Van Holten, et al.: "Treatment with recombinant interferon-β reduces inflammation and slows cartilage destruction in the collagen-induced arthritis model of rheumatoid arthritis" Arthritis Res.: Ther. 2004.
EP 09833924.5 Extented European Search Report, dated Mar. 5, 2013.

* cited by examiner

Results are expressed as the mean ± SEM.

* p=0.04,  p=0.04, * p=0.02, ****p=0.005, Unpaired t-test.

SEQUENCE LISTING

<160> NUMBER OF SEQ ID NOS: 46

<210> SEQ ID NO 1
<211> LENGTH: 140
<212> TYPE: PRT

```
<213> ORGANISM: artificial
<220> FEATURE:
<223> OTHER INFORMATION: amino acid sequence of heavy chain variable
      region

<400> SEQUENCE: 1

Met Glu Leu Ile Met Leu Phe Leu Leu Ser Gly Thr Ala Gly Val His
1               5                   10                  15

Ser Glu Val Gln Leu Gln Gln Ser Gly Pro Glu Leu Val Lys Pro Gly
            20                  25                  30

Ala Ser Val Lys Ile Ser Cys Lys Ala Ser Gly Tyr Thr Phe Thr Asp
        35                  40                  45

Tyr Asn Ile His Trp Val Lys Gln Ser His Gly Lys Ser Leu Asp Trp
    50                  55                  60

Ile Gly Tyr Ile Ala Pro Tyr Ser Gly Gly Thr Gly Tyr Asn Gln Glu
65                  70                  75                  80

Phe Lys Asn Arg Ala Thr Leu Thr Val Asp Lys Ser Ser Thr Ala
                85                  90                  95

Tyr Met Glu Leu Arg Ser Leu Thr Ser Asp Asp Ser Ala Val Tyr Tyr
            100                 105                 110

Cys Ala Arg Arg Asp Arg Phe Pro Tyr Tyr Phe Asp Tyr Trp Gly Gln
        115                 120                 125

Gly Thr Thr Leu Arg Val Ser Ser Val Ser Gly Ser
    130                 135                 140

<210> SEQ ID NO 2
<211> LENGTH: 150
<212> TYPE: PRT
<213> ORGANISM: artificial
<220> FEATURE:
<223> OTHER INFORMATION: amino acid sequence of light chain variable
      region

<400> SEQUENCE: 2

Met Gly Phe Lys Met Glu Ser Gln Ile Gln Val Phe Val Tyr Met Leu
1               5                   10                  15

Leu Trp Leu Ser Gly Val Asp Gly Asp Ile Val Met Ile Gln Ser Gln
            20                  25                  30

Lys Phe Val Ser Thr Ser Val Gly Asp Arg Val Asn Ile Thr Cys Lys
        35                  40                  45

Ala Ser Gln Asn Val Gly Ser Asn Val Ala Trp Leu Gln Gln Lys Pro
    50                  55                  60

Gly Gln Ser Pro Lys Thr Leu Ile Tyr Ser Ala Ser Tyr Arg Ser Gly
65                  70                  75                  80

Arg Val Pro Asp Arg Phe Thr Gly Ser Gly Ser Gly Thr Asp Phe Ile
                85                  90                  95

Leu Thr Ile Thr Thr Val Gln Ser Glu Asp Leu Ala Glu Tyr Phe Cys
            100                 105                 110

Gln Gln Phe Asn Arg Ser Pro Leu Thr Phe Gly Ser Gly Thr Lys Leu
        115                 120                 125

Glu Leu Lys Arg Ala Asp Ala Ala Pro Thr Val Ser Ile Phe Pro Pro
    130                 135                 140

Ser Ser Lys Gly Glu Phe
145                 150

<210> SEQ ID NO 3
<211> LENGTH: 117
<212> TYPE: PRT
```

```
<213> ORGANISM: artificial
<220> FEATURE:
<223> OTHER INFORMATION: amino acid sequence of heavy chain variable
      region

<400> SEQUENCE: 3

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Asn Trp Val Arg Gln Ala Pro Gly Lys Gly Leu Glu Trp Val
        35                  40                  45

Ser Gly Ile Glu Asn Lys Tyr Ala Gly Gly Ala Thr Tyr Tyr Ala Ala
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg Gly Phe Gly Thr Asp Phe Trp Gly Gln Gly Thr Leu
            100                 105                 110

Val Thr Val Ser Ser
            115

<210> SEQ ID NO 4
<211> LENGTH: 105
<212> TYPE: PRT
<213> ORGANISM: artificial
<220> FEATURE:
<223> OTHER INFORMATION: amino acid sequence of light chain variable
      region

<400> SEQUENCE: 4

Asp Ile Glu Leu Thr Gln Pro Pro Ser Val Ser Val Ala Pro Gly Gln
1               5                   10                  15

Thr Ala Arg Ile Ser Cys Ser Gly Asp Ser Ile Gly Lys Lys Tyr Ala
            20                  25                  30

Tyr Trp Tyr Gln Gln Lys Pro Gly Gln Ala Pro Val Leu Val Ile Tyr
        35                  40                  45

Lys Lys Arg Pro Ser Gly Ile Pro Glu Arg Phe Ser Gly Ser Asn Ser
    50                  55                  60

Gly Asn Thr Ala Thr Leu Thr Ile Ser Gly Thr Gln Ala Glu Asp Glu
65                  70                  75                  80

Ala Asp Tyr Tyr Cys Ser Ala Trp Gly Lys Gly Met Val Phe Gly Gly
                85                  90                  95

Gly Thr Lys Leu Thr Val Leu Gly Gln
            100                 105

<210> SEQ ID NO 5
<211> LENGTH: 10
<212> TYPE: PRT
<213> ORGANISM: artificial
<220> FEATURE:
<223> OTHER INFORMATION: amino acid sequence of Homo sapiens CDR3
      (H-CDR3)

<400> SEQUENCE: 5

Ser Gly Leu Ile Phe Asp Tyr Trp Leu Asp
1               5                   10

<210> SEQ ID NO 6
```

```
<211> LENGTH: 10
<212> TYPE: PRT
<213> ORGANISM: artificial
<220> FEATURE:
<223> OTHER INFORMATION: amino acid sequence of Homo sapiens CDR3
      (H-CDR3)

<400> SEQUENCE: 6

Ser Gly Leu Ile Ile Asp Ala Leu Ser Pro
1               5                   10

<210> SEQ ID NO 7
<211> LENGTH: 10
<212> TYPE: PRT
<213> ORGANISM: artificial
<220> FEATURE:
<223> OTHER INFORMATION: amino acid sequence of Homo sapiens CDR3
      (H-CDR3)

<400> SEQUENCE: 7

Thr Ser Leu Met Ser Ile Tyr Phe Asp Tyr
1               5                   10

<210> SEQ ID NO 8
<211> LENGTH: 10
<212> TYPE: PRT
<213> ORGANISM: artificial
<220> FEATURE:
<223> OTHER INFORMATION: amino acid sequence of Homo sapiens CDR3
      (H-CDR3)

<400> SEQUENCE: 8

Ser Gly Leu Leu Phe Leu Tyr Phe Asp Tyr
1               5                   10

<210> SEQ ID NO 9
<211> LENGTH: 10
<212> TYPE: PRT
<213> ORGANISM: artificial
<220> FEATURE:
<223> OTHER INFORMATION: amino acid sequence of Homo sapiens CDR3
      (H-CDR3)

<400> SEQUENCE: 9

Ser Gly Leu Ile Asn Leu Gly Met His Pro
1               5                   10

<210> SEQ ID NO 10
<211> LENGTH: 10
<212> TYPE: PRT
<213> ORGANISM: artificial
<220> FEATURE:
<223> OTHER INFORMATION: amino acid sequence of Homo sapiens CDR3
      (H-CDR3)

<400> SEQUENCE: 10

Ser Gly Leu Ile Phe Asp Ala Leu Arg Asp
1               5                   10

<210> SEQ ID NO 11
<211> LENGTH: 10
<212> TYPE: PRT
<213> ORGANISM: artificial
<220> FEATURE:
<223> OTHER INFORMATION: amino acid sequence of Homo sapiens CDR3
      (H-CDR3)

<400> SEQUENCE: 11
```

```
Ser Gly Leu Ile Phe Asp Lys Leu Thr Ser
1               5                   10

<210> SEQ ID NO 12
<211> LENGTH: 10
<212> TYPE: PRT
<213> ORGANISM: artificial
<220> FEATURE:
<223> OTHER INFORMATION: amino acid sequence of Homo sapiens CDR3
      (H-CDR3)

<400> SEQUENCE: 12

Ser Gly Leu Ile Asn Leu His Phe Asp Thr
1               5                   10

<210> SEQ ID NO 13
<211> LENGTH: 10
<212> TYPE: PRT
<213> ORGANISM: artificial
<220> FEATURE:
<223> OTHER INFORMATION: amino acid sequence of Homo sapiens CDR3
      (H-CDR3)

<400> SEQUENCE: 13

Ser Thr His Phe Ser Ala Tyr Phe Asp Tyr
1               5                   10

<210> SEQ ID NO 14
<211> LENGTH: 10
<212> TYPE: PRT
<213> ORGANISM: artificial
<220> FEATURE:
<223> OTHER INFORMATION: amino acid sequence of Homo sapiens CDR3
      (H-CDR3)

<400> SEQUENCE: 14

Ser Gly Leu Ile Met Asp Lys Leu Asp Asn
1               5                   10

<210> SEQ ID NO 15
<211> LENGTH: 10
<212> TYPE: PRT
<213> ORGANISM: artificial
<220> FEATURE:
<223> OTHER INFORMATION: amino acid sequence of Homo sapiens CDR3
      (H-CDR3)

<400> SEQUENCE: 15

Ser Gly Leu Ile Ile Asp Asn Leu Asn Pro
1               5                   10

<210> SEQ ID NO 16
<211> LENGTH: 10
<212> TYPE: PRT
<213> ORGANISM: artificial
<220> FEATURE:
<223> OTHER INFORMATION: amino acid sequence of Homo sapiens CDR3
      (H-CDR3)

<400> SEQUENCE: 16

Ser Gly Leu Ile Ala Val Tyr Phe Asp Tyr
1               5                   10

<210> SEQ ID NO 17
<211> LENGTH: 5
<212> TYPE: PRT
<213> ORGANISM: artificial
<220> FEATURE:
```

```
<223> OTHER INFORMATION: amino acid sequence of heavy CDR1 (H-CDR1)

<400> SEQUENCE: 17

Asp Tyr Leu Leu His
1               5

<210> SEQ ID NO 18
<211> LENGTH: 17
<212> TYPE: PRT
<213> ORGANISM: artificial
<220> FEATURE:
<223> OTHER INFORMATION: amino acid sequence of heavy CDR2 (H-CDR2)

<400> SEQUENCE: 18

Trp Leu Asn Pro Tyr Ser Gly Asp Thr Asn Tyr Ala Gln Lys Phe Gln
1               5                   10                  15

Gly

<210> SEQ ID NO 19
<211> LENGTH: 11
<212> TYPE: PRT
<213> ORGANISM: artificial
<220> FEATURE:
<223> OTHER INFORMATION: amino acid sequence of light CDR1 (L-CDR1)

<400> SEQUENCE: 19

Arg Ala Ser Gln Asn Ile Arg Asn Ile Leu Asn
1               5                   10

<210> SEQ ID NO 20
<211> LENGTH: 7
<212> TYPE: PRT
<213> ORGANISM: artificial
<220> FEATURE:
<223> OTHER INFORMATION: amino acid sequence of light CDR2 (L-CDR2)

<400> SEQUENCE: 20

Ala Ala Ser Asn Leu Gln Ser
1               5

<210> SEQ ID NO 21
<211> LENGTH: 9
<212> TYPE: PRT
<213> ORGANISM: artificial
<220> FEATURE:
<223> OTHER INFORMATION: amino acid sequence of light CDR3 (L-CDR3)

<400> SEQUENCE: 21

Gln Gln Ser Tyr Ser Met Pro Arg Thr
1               5

<210> SEQ ID NO 22
<211> LENGTH: 12
<212> TYPE: PRT
<213> ORGANISM: artificial
<220> FEATURE:
<223> OTHER INFORMATION: amino acid sequence of light CDR1 (L-CDR1)

<400> SEQUENCE: 22

Arg Ala Ser His Arg Val Ser Ser Asn Tyr Leu Ala
1               5                   10

<210> SEQ ID NO 23
<211> LENGTH: 7
<212> TYPE: PRT
<213> ORGANISM: artificial
```

```
<220> FEATURE:
<223> OTHER INFORMATION: amino acid sequence of light CDR2 (L-CDR2)

<400> SEQUENCE: 23

Gly Ala Ser Asn Arg Ala Thr
1               5

<210> SEQ ID NO 24
<211> LENGTH: 9
<212> TYPE: PRT
<213> ORGANISM: artificial
<220> FEATURE:
<223> OTHER INFORMATION: amino acid sequence of light CDR3 (L-CDR3)

<400> SEQUENCE: 24

Gln Gln Tyr Ala Ser Ser Pro Val Thr
1               5

<210> SEQ ID NO 25
<211> LENGTH: 10
<212> TYPE: PRT
<213> ORGANISM: artificial
<220> FEATURE:
<223> OTHER INFORMATION: amino acid sequence of heavy CDR3 (H-CDR3)

<400> SEQUENCE: 25

Gly Tyr Ile Phe Pro Thr Phe Ala Leu His
1               5                   10

<210> SEQ ID NO 26
<211> LENGTH: 16
<212> TYPE: PRT
<213> ORGANISM: artificial
<220> FEATURE:
<223> OTHER INFORMATION: amino acid sequence of heavy CDR2 (H-CDR2)

<400> SEQUENCE: 26

Ser Ile Asn Thr Ala Ser Gly Lys Thr Lys Phe Ser Thr Lys Phe Gln
1               5                   10                  15

<210> SEQ ID NO 27
<211> LENGTH: 13
<212> TYPE: PRT
<213> ORGANISM: artificial
<220> FEATURE:
<223> OTHER INFORMATION: amino acid sequence of heavy CDR3 (H-CDR3)

<400> SEQUENCE: 27

Asp Arg Phe Gln Asn Ile Met Ala Thr Ile Leu Asp Val
1               5                   10

<210> SEQ ID NO 28
<211> LENGTH: 11
<212> TYPE: PRT
<213> ORGANISM: artificial
<220> FEATURE:
<223> OTHER INFORMATION: amino acid sequence of heavy CDR3 (H-CDR3)

<400> SEQUENCE: 28

Val Gly Ser Phe Ser Gly Ile Ala Tyr Arg Pro
1               5                   10

<210> SEQ ID NO 29
<211> LENGTH: 11
<212> TYPE: PRT
<213> ORGANISM: artificial
<220> FEATURE:
```

```
<223> OTHER INFORMATION: amino acid sequence of heavy CDR3 (H-CDR3)

<400> SEQUENCE: 29

Val Gly Ser Phe Ser Gly Pro Ala Leu Arg Pro
1               5                   10

<210> SEQ ID NO 30
<211> LENGTH: 11
<212> TYPE: PRT
<213> ORGANISM: artificial
<220> FEATURE:
<223> OTHER INFORMATION: amino acid sequence of heavy CDR3 (H-CDR3)

<400> SEQUENCE: 30

Val Gly Ser Phe Ser Pro Pro Thr Tyr Gly Tyr
1               5                   10

<210> SEQ ID NO 31
<211> LENGTH: 11
<212> TYPE: PRT
<213> ORGANISM: artificial
<220> FEATURE:
<223> OTHER INFORMATION: amino acid sequence of heavy CDR3 (H-CDR3)

<400> SEQUENCE: 31

Val Gly Ser Phe Ser Gly Tyr Pro Tyr Arg Pro
1               5                   10

<210> SEQ ID NO 32
<211> LENGTH: 11
<212> TYPE: PRT
<213> ORGANISM: artificial
<220> FEATURE:
<223> OTHER INFORMATION: amino acid sequence of heavy CDR3 (H-CDR3)

<400> SEQUENCE: 32

Val Gly Ser Phe Ser Pro Leu Thr Leu Gly Leu
1               5                   10

<210> SEQ ID NO 33
<211> LENGTH: 11
<212> TYPE: PRT
<213> ORGANISM: artificial
<220> FEATURE:
<223> OTHER INFORMATION: amino acid sequence of heavy CDR3 (H-CDR3)

<400> SEQUENCE: 33

Val Gly Ser Phe Ser Gly Pro Val Tyr Gly Leu
1               5                   10

<210> SEQ ID NO 34
<211> LENGTH: 11
<212> TYPE: PRT
<213> ORGANISM: artificial
<220> FEATURE:
<223> OTHER INFORMATION: amino acid sequence of heavy CDR3 (H-CDR3)

<400> SEQUENCE: 34

Val Gly Ser Phe Ser Pro Pro Ala Tyr Arg Pro
1               5                   10

<210> SEQ ID NO 35
<211> LENGTH: 11
<212> TYPE: PRT
<213> ORGANISM: artificial
<220> FEATURE:
<223> OTHER INFORMATION: amino acid sequence of heavy CDR3 (H-CDR3)
```

```
<400> SEQUENCE: 35

Val Gly Ser Phe Ser Pro Val Thr Tyr Gly Leu
1               5                   10

<210> SEQ ID NO 36
<211> LENGTH: 11
<212> TYPE: PRT
<213> ORGANISM: artificial
<220> FEATURE:
<223> OTHER INFORMATION: amino acid sequence of heavy CDR3 (H-CDR3)

<400> SEQUENCE: 36

Val Gly Ser Phe Ser Gly Leu Ala Tyr Arg Pro
1               5                   10

<210> SEQ ID NO 37
<211> LENGTH: 11
<212> TYPE: PRT
<213> ORGANISM: artificial
<220> FEATURE:
<223> OTHER INFORMATION: amino acid sequence of heavy CDR3 (H-CDR3)

<400> SEQUENCE: 37

Val Gly Ser Phe Ser Pro Ile Thr Tyr Gly Leu
1               5                   10

<210> SEQ ID NO 38
<211> LENGTH: 11
<212> TYPE: PRT
<213> ORGANISM: artificial
<220> FEATURE:
<223> OTHER INFORMATION: amino acid sequence of heavy CDR3 (H-CDR3)

<400> SEQUENCE: 38

Val Gly Ser Phe Ser Gly Trp Ala Phe Asp Tyr
1               5                   10

<210> SEQ ID NO 39
<211> LENGTH: 11
<212> TYPE: PRT
<213> ORGANISM: artificial
<220> FEATURE:
<223> OTHER INFORMATION: amino acid sequence of heavy CDR3 (H-CDR3)

<400> SEQUENCE: 39

Val Gly Ser Phe Ser Gly Trp Ala Phe Asp Tyr
1               5                   10

<210> SEQ ID NO 40
<211> LENGTH: 11
<212> TYPE: PRT
<213> ORGANISM: artificial
<220> FEATURE:
<223> OTHER INFORMATION: amino acid sequence of heavy CDR3 (H-CDR3)

<400> SEQUENCE: 40

Leu Gly Ser Val Thr Ala Trp Ala Phe Asp Tyr
1               5                   10

<210> SEQ ID NO 41
<211> LENGTH: 11
<212> TYPE: PRT
<213> ORGANISM: artificial
<220> FEATURE:
<223> OTHER INFORMATION: amino acid sequence of heavy CDR3 (H-CDR3)
```

```
<400> SEQUENCE: 41

Ala Gly Ser Ile Pro Gly Trp Ala Phe Asp Tyr
1               5                   10

<210> SEQ ID NO 42
<211> LENGTH: 11
<212> TYPE: PRT
<213> ORGANISM: artificial
<220> FEATURE:
<223> OTHER INFORMATION: amino acid sequence of heavy CDR3 (H-CDR3)

<400> SEQUENCE: 42

Val Gly Ser Phe Ser Pro Leu Thr Met Gly Leu
1               5                   10

<210> SEQ ID NO 43
<211> LENGTH: 11
<212> TYPE: PRT
<213> ORGANISM: artificial
<220> FEATURE:
<223> OTHER INFORMATION: amino acid sequence of heavy CDR3 (H-CDR3)

<400> SEQUENCE: 43

Val Gly Ser Phe Ser Pro Leu Thr Met Gly Leu
1               5                   10

<210> SEQ ID NO 44
<211> LENGTH: 11
<212> TYPE: PRT
<213> ORGANISM: artificial
<220> FEATURE:
<223> OTHER INFORMATION: amino acid sequence of heavy CDR3 (H-CDR3)

<400> SEQUENCE: 44

Val Gly Ser Phe Ser Gly Pro Ala Leu His Leu
1               5                   10

<210> SEQ ID NO 45
<211> LENGTH: 11
<212> TYPE: PRT
<213> ORGANISM: artificial
<220> FEATURE:
<223> OTHER INFORMATION: amino acid sequence of heavy CDR3 (H-CDR3)

<400> SEQUENCE: 45

Val Gly Ser Val Ser Arg Ile Thr Tyr Gly Phe
1               5                   10

<210> SEQ ID NO 46
<211> LENGTH: 11
<212> TYPE: PRT
<213> ORGANISM: artificial
<220> FEATURE:
<223> OTHER INFORMATION: amino acid sequence of heavy CDR3 (H-CDR3)

<400> SEQUENCE: 46

Val Gly Ser Phe Ser Pro Leu Thr Leu Gly Leu
1               5                   10
```

OSTEOARTHRITIS TREATMENT

This application claims the benefit of U.S. Provisional Application No. 61/139,679, filed Dec. 22, 2008, and U.S. Provisional Application No. 61/164,486, filed Mar. 30, 2009, which are both incorporated by reference in their entireties.

FIELD OF THE INVENTION

The present invention relates generally to a method for the treatment and/or prophylaxis of osteoarthritis (OA). In accordance with the present invention, an antagonist of GM-CSF can be effective in the treatment of osteoarthritis. An antagonist of GM-CSF includes, but is not limited to, an antibody that is specific for GM-CSF or the GM-CSF receptor. The present invention further provides transgenic animals, such as a GM-CSF knock-out mouse, useful for testing antagonists in certain disease models.

BACKGROUND OF THE INVENTION

Osteoarthritis (OA), also known as degenerative arthritis, is a disease most prevalent in the old and obese. OA is a disease of the articular joints, but, unlike rheumatoid arthritis (RA), the disease is not systemic, usually affecting only one or a few joints. The disease leads to total destruction of the articular cartilage, sclerosis of the underlying bones, and osteophyte formation, resulting in loss of movement and pain. The ultimate result is often the need for a total joint replacement.

OA affects about ~21 million people in the US, comprises 25% of all primary care physician visits and accounts for 50% of all NSAID (non steroidal anti inflammatory drugs) prescriptions. There is currently no treatment available which slows or halts disease progression; today's drugs merely treat the symptoms. The incidence and severity of the disease increase with age. By the age of 65, 80% of Americans show radiographic evidence of OA though only 60% of them will be symptomatic. 65% of all joint disease by the age of 65 are OA. In 2006, there were 735,000 OA-related US hospitalizations.

Current OA drugs treat the symptoms of OA rather than the disease itself. Commonly used drugs in the treatment of OA include Non-steroidal anti-inflammatory drugs (NSAIDs), such as diacerin, voltaren. mobic and arthrotec (generic names: diclofenac, misoprostol, meloxicam). NSAIDs are mainly oral compounds which act by inhibiting prostaglandin synthesis in the central nervous system (CNS). Other commonly used drugs include non-narcotic analgesics, such as ultram (tramadol), COX-2 inhibitors, such as celebrax and arcoxia (celecoxib, etoricoxib), narcotic analgesiscs, such as duragesic (dextropropoxyphene fentanyl), hyaluraonic acids, such as suparts, hyalgan, orthovisc and synvisc (Hylan G-F20), and corticosteroids, such as predinisolone and methyl predinisolone. Present treatments for OA intend to obviate the need for surgery through tissue engineering, such as chondrocyte transplantation; however, these treatments are-only applicable for the treatment of last stage OA. Other approaches in the treatment of OA that are considered include prolotherapy, in which an irritant, such as dextrose, is injected into the affected joint, thereby causing an acute inflammatory reaction, but also strengthening and hopefully healing the tissues, ligaments, tendons, and cartilage. There is, thus, a high unmet medical need for the treatment of OA.

Some cytokines are known to be involved in osteoarthritis (Blom et al., Current Drug Targets (2008) 8:283). A few cytokines, such as IL-1, a 'destructive' cytokine, and the anabolic growth factor transforming growth factor β (TGF β) are considered as potential drug targets.

Granulocyte macrophage colony-stimulating factor (GM-CSF) is a cytokine that functions as a white blood cell growth factor. GM-CSF stimulates stem cells to produce granulocytes (neutrophils, eosinophils, and basophils) and monocytes. Monocytes exit the circulation and migrate into tissue, whereupon they mature into macrophages. It is, thus, part of the natural immune/inflammatory cascade, by which activation of a small number of macrophages can rapidly lead to an increase in their numbers, a process crucial for fighting infection. The active form of GM-CSF is found extracellularly as a homodimer. In particular, GM-CSF has been identified as an inflammatory mediator in autoimmune disorders, like rheumatoid arthritis (RA), leading to an increased production of pro-inflammatory cytokines, chemokines and proteases and, thereby, ultimately to articular destruction.

WO 06/0234412 discloses numerous biomarkers for osteoarthritis, which were identified by protein microarrays. One of the biomarkers identified is GM-CSF, for which a four-fold up-regulation is reported in OA tissue. However, no indication or suggestion is provided that GM-CSF may also be a point for therapeutic intervention, and a mere four-fold up-regulation in OA tissue, as identified with the technology disclosed in WO 06/0234412, also does not suggest the same. In a related vein, Devalaraja et al (US20020141994A1) cursorily mention OA among a long list of potentially suitable indications suitable for treatment with antagonists of colony stimulating factors. The list of indications includes atherosclerosis, sepsis, asthma, autoimmune disease, osteoporosis and rheumatoid arthritis. Besides other colony stimulating factors, such as M-CSF and G-CSF, GM-CSF is one of the colony stimulating factors mentioned in Devalaraja et al. Indeed, Devalaraja et al. include no data or other insights as to why antagonizing GM-CSF would be appropriate to treat a subject suffering from OA.

SUMMARY OF THE INVENTION

The present invention, for the first time, demonstrates that GM-CSF is a valid target for the treatment of OA. This finding is new, and the prior art does not teach, suggest or provide any rational for such a point of intervention in the treatment of OA. Accordingly, the invention provides, e.g., a method for the treatment of osteoarthritis in a subject, said method comprising the step of administering an effective amount of a GM-CSF antagonist to said subject.

In another aspect, the present invention contemplates a method for the prophylaxis of osteoarthritis in a subject, said method comprising the step of administering an effective amount of GM-CSF antagonist to said subject.

In another aspect, the present invention is directed to a composition comprising a GM-CSF antagonist capable of antagonizing the ability of GM-CSF from activating, proliferating, inducing growth and/or survival of cells in a subject suffering from osteoarthritis, or being suspected of suffering from osteoarthritis, said composition further comprising one or more pharmaceutically acceptable carriers and/or diluents.

In another aspect, the present invention is directed to a composition comprising a GM-CSF antagonist useful in the treatment of osteoarthritis, said composition further comprising one or more pharmaceutically acceptable carriers and/or diluents.

In particular aspects of the present invention, the GM-CSF antagonist is an antibody specific for GM-CSF.

In alternative aspects of the present invention, the GM-CSF antagonist is an antibody specific for the GM-CSF receptor.

In other aspects, the present invention is directed to the use of a GM-CSF antagonist in the preparation of a medicament in the treatment of osteoarthritis.

In other aspects, the present invention provides GM-CSF antagonists for the treatment of osteoarthritis.

Throughout this specification, unless the context requires otherwise, the words "comprise", "have" and "include" and their respective variations such as "comprises", "comprising", "has", "having", "includes" and "including" will be understood to imply the inclusion of a stated element or integer or group of elements or integers but not the exclusion of any other element or integer or group of elements or integers.

DETAILED DESCRIPTION OF THE INVENTION

Figure 1:
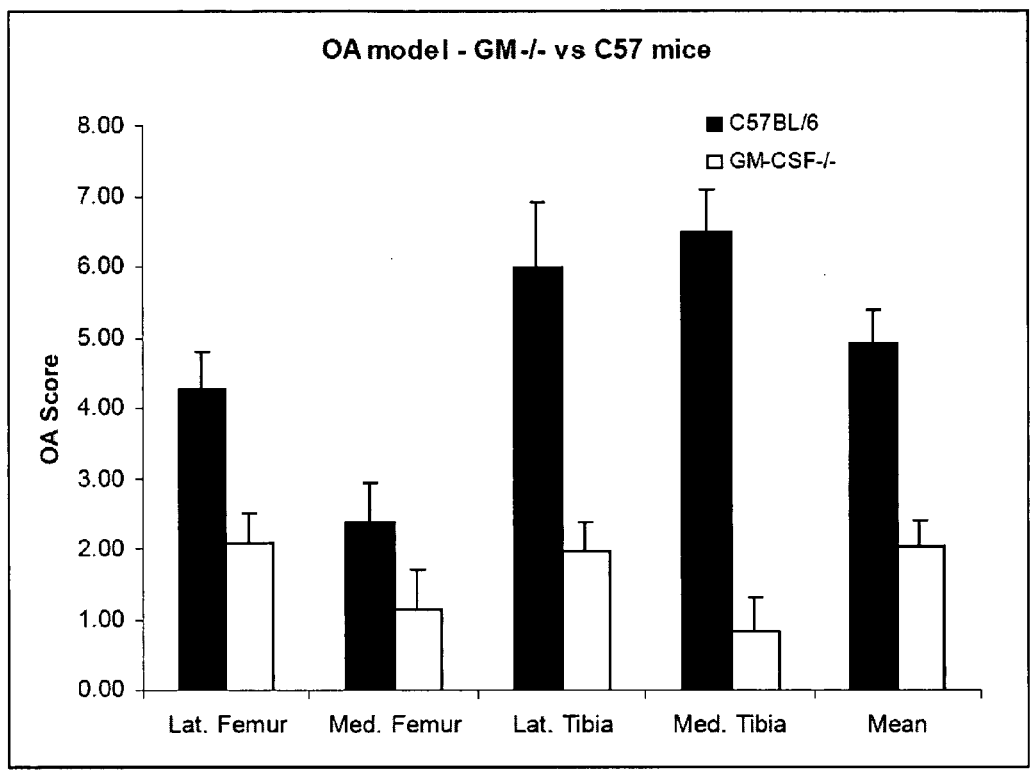
FIG. 1 shows quantitative data for joint damage in different regions assessed by histological scoring. The experimental set-up and the scoring system are described in Example 2. "Lat." stands for lateral, "Med." stands for medial. Statistical analysis was performed via Mann-Whitney. The data are statistically significant for Lat. Femur (p=0.02), Lat Tibia (p=0.003), Med, Tibia (p=0.001), and over all regions (Mean; p=0.002).

The present invention demonstrates that GM-CSF is a valid target for the treatment of OA. In this respect, the invention provides, in one aspect, methods of using a GM-CSF antagonist to bring about a prophylactic or therapeutic benefit in the field of OA.

The present invention provides therapeutic methods comprising the administration of a therapeutically effective amount of a GM-CSF antagonist to a subject in need of such treatment. A "therapeutically effective amount" or "effective amount", as used herein, refers to the amount of a GM-CSF antagonist necessary to elicit the desired biological response. In accordance with the subject invention, the therapeutic effective amount is the amount of a GM-CSF antagonist necessary to treat and/or prevent osteoarthritis.

"GM-CSF antagonists", as used herein, includes GM-CSF antagonists in its broadest sense; any molecule which inhibits the activity or function of GM-CSF, or which by any other way exerts a therapeutic effect on GM-CSF is included. The term GM-CSF antagonists includes, but is not limited to, antibodies specifically binding to GM-CSF, inhibitory nucleic acids specific for GM-CSF or small organic molecules specific for GM-CSF. Also within the meaning of the term GM-CSF antagonist are antibodies specifically binding to the GM-CSF receptor, inhibitory nucleic acids specific for the GM-CSF receptor or small organic molecules specific for the GM-CSF receptor.

Inhibitory nucleic acids include, but are not limited to, antisense DNA, triplex-forming oligonucleotides, external guide sequences, siRNA and microRNA. Useful inhibitory nucleic acids include those that reduce the expression of RNA encoding GM-CSF by at least 20, 30, 40, 50, 60, 70, 80, 90 or 95 percent compared to controls. Inhibitory nucleic acids and methods of producing them are well known in the art siRNA design software is available.

Small organic molecules (SMOLs) specific for GM-CSF or the GM-CSF receptor may be identified via natural product screening or screening of chemical libraries. Typically the molecular weight of SMOLs is below 500 Dalton, more typically from 160 to 480 Daltons. Other typical properties of SMOLs are one or more of the following:

The partition coefficient log P is in the range from −0.4 to +5.6

The molar refractivity is from 40 to 130

The number of atoms is from 20 to 70

For reviews see Ghose et al, *J Combin Chem:* 1:55-68, 1999 and Lipinski et al, *Adv Drug Del Rev* 23:3-25, 1997.

Preferably, a GM-CSF antagonist for use in the present invention is an antibody specific for GM-CSF or specific for the GM-CSF receptor. Such an antibody may be of any type, such as a murine, a rat, a chimeric, a humanized or a human antibody. A "human" antibody or functional human antibody fragment is hereby defined as one that is not chimeric (e.g., not "humanized") and not from (either in whole or in part) a non-human species. A human antibody or functional antibody fragment can be derived from a human or can be a synthetic human antibody. A "synthetic human antibody" is defined herein as an antibody having a sequence derived, in whole or in part, in silico from synthetic sequences that are based on the analysis of known human antibody sequences. In silico design of a human antibody sequence or fragment thereof can be achieved, for example, by analyzing a database of human antibody or antibody fragment sequences and devising a polypeptide sequence utilizing the data obtained therefrom. Another example of a human antibody or functional antibody fragment is one that is encoded by a nucleic acid isolated from a library of antibody sequences of human origin (i.e., such library being based on antibodies taken from a human natural source).

A "humanized antibody" or functional humanized antibody fragment is defined herein as one that is (i) derived from a non-human source (e.g., a transgenic mouse which bears a heterologous immune system), which antibody is based on a human germline sequence; or (ii) chimeric, wherein the variable domain is derived from a non-human origin and the constant domain is derived from a human origin or (iii) CDR-grafted, wherein the CDRs of the variable domain are from a non-human origin, while one or more frameworks of the variable domain are of human origin and the constant domain (if any) is of human origin.

The term "chimeric antibody" or functional chimeric antibody fragment is defined herein as an antibody molecule which has constant antibody regions derived from, or corresponding to, sequences found in one species and variable antibody regions derived from another species. Preferably, the constant antibody regions are derived from, or corresponding to, sequences found in humans, e.g. in the human germ line or somatic cells, and the variable antibody regions (e.g. VH, VL, CDR or FR regions) are derived from sequences found in a non-human animal, e.g. a mouse, rat, rabbit or hamster.

As used herein, an antibody "binds specifically to", "specifically binds to", is "specific to/for" or "specifically recognizes" an antigen (here, GM-CSF or, alternatively, the GM-CSF receptor) if such antibody is able to discriminate between such antigen and one or more reference antigen(s), since binding specificity is not an absolute, but a relative property. The reference antigen(s) may be one or more closely related antigen(s), which are used as reference points, e.g. IL3, IL5, IL-4, IL13 or M-CSF. In its most general form (and when no defined reference is mentioned), "specific binding" is referring to the ability of the antibody to discriminate between the antigen of interest and an unrelated antigen, as determined, for example, in accordance with one of the following methods. Such methods comprise, but are not limited to Western blots, ELISA-, RIA-, ECL-, IRMA-tests and peptide scans. For example, a standard ELISA assay can be carried out. The scoring may be carried out by standard color development (e.g. secondary antibody with horseradish peroxide and tetramethyl benzidine with hydrogenperoxide). The reaction in certain wells is scored by the optical density, for example, at 450 nm. Typical background (=negative reaction) may be 0.1 OD; typical positive reaction may be 1 OD. This means the difference positive/negative can be more than 10-fold. Typically, determination of binding specificity is performed by using not a single reference antigen, but a set of about three to five unrelated antigens, such as milk powder, BSA, transferrin or the like. Additionally, "specific binding" may relate to the ability of an antibody to discriminate between different parts of its target antigen, e.g. different domains or regions of GM-CSF or the GM-CSF receptor, or between one or more key amino acid residues or stretches of amino acid residues of GM-CSF or the GM-CSF receptor.

Also, as used herein, an "immunoglobulin" (Ig) hereby is defined as a protein belonging to the class IgG, IgM, IgE, IgA, or IgD (or any subclass thereof), and includes all conventionally known antibodies and functional fragments thereof. A "functional fragment" of an antibody/immunoglobulin hereby is defined as a fragment of an antibody/immunoglobulin (e.g., a variable region of an IgG) that retains the antigen-binding region. An "antigen-binding region" of an antibody typically is found in one or more hypervariable region(s) of an antibody, i.e., the CDR-1, -2, and/or -3 regions; however, the variable "framework" regions can also play an important role in antigen binding, such as by providing a scaffold for the CDRs. Preferably, the "antigen-binding region" comprises at least amino acid residues 4 to 103 of the variable light (VL) chain and 5 to 109 of the variable heavy (VH) chain, more preferably amino acid residues 3 to 107 of VL and 4 to 111 of VH, and particularly preferred are the complete VL and VH chains (amino acid positions 1 to 109 of VL and 1 to 113 of VH; numbering according to WO 97/08320). A preferred class of immunoglobulins for use in the present invention is IgG. "Functional fragments" of the invention include the domain of a F(ab')$_2$ fragment, a Fab fragment, scFv or constructs comprising single immunoglobulin variable domains or single domain antibody polypeptides, e.g. single heavy chain variable domains or single light chain variable domains. The F(ab')$_2$ or Fab may be engineered to minimize or completely remove the intermolecular disulphide interactions that occur between the $C_{H1}$ and $C_L$ domains.

An antibody of the invention may be derived from a recombinant antibody library that is based on amino acid sequences that have been designed in silico and encoded by nucleic acids that are synthetically created. In silico design of an antibody sequence is achieved, for example, by analyzing a database of human sequences and devising a polypeptide sequence utilizing the data obtained therefrom. Methods for designing and obtaining in silico-created sequences are described, for example, in Knappik et al, *J. Mol. Biol.* 296:57, 2000; Krebs et al, *J. Immunol. Methods.* 254:67, 2001; Rothe et al, *J. Mol. Biol.* 376:1182, 2008 and U.S. Pat. No. 6,300,064 issued to Knappik et al 2000 supra, which hereby are incorporated by reference in their entirety.

Any antibody specific for GM-CSF may be used with the present invention. Exemplary antibodies are disclosed in U.S. Ser. No. 11/914,599, which is incorporated by reference in its entirety. Other exemplary antibodies include antibodies comprising an amino acid sequence of a heavy chain variable region as depicted in SEQ ID NO:1 or an amino acid sequence of a light chain variable region as depicted in SEQ ID NO:2. Yet other exemplary antibodies include antibodies which are derived from antibodies comprising a heavy chain variable region as depicted in SEQ ID NO:1 or an amino acid sequence of a light chain variable region as depicted in SEQ ID NO:2. Yet other exemplary antibodies include antibodies which have the same specificity and/or bind to the same epitope as antibodies comprising a heavy chain variable region as depicted in SEQ ID NO:1 or an amino acid sequence of a light chain variable region as depicted in SEQ ID NO:2. Yet other exemplary antibodies include antibodies which comprise a heavy chain variable region which is at least 70%, at least 80%, at least 90% or at least 95% homologous to the sequence depicted in SEQ ID NO:1. Yet other exemplary antibodies include antibodies which comprise a light chain variable region which is at least 70%, at least 80%, at least 90% or at least 95% homologous to the sequence depicted in SEQ ID NO:2.

```
SEQ ID NO: 1:
Met Glu Leu Ile Met Leu Phe Leu Leu Ser Gly Thr Ala Gly Val His

Ser Glu Val Gln Leu Gln Ser Gly Pro Glu Leu Val Lys Pro Gly

Ala Ser Val Lys Ile Ser Cys Lys Ala Ser Gly Tyr Thr Phe Thr Asp

Tyr Asn Ile His Trp Val Lys Gln Ser His Gly Lys Ser Leu Asp Trp

Ile Gly Tyr Ile Ala Pro Tyr Ser Gly Gly Thr Gly Tyr Asn Gln Glu
```

-continued
Phe Lys Asn Arg Ala Thr Leu Thr Val Asp Lys Ser Ser Ser Thr Ala

Tyr Met Glu Leu Arg Ser Leu Thr Ser Asp Asp Ser Ala Val Tyr Tyr

Cys Ala Arg Arg Asp Arg Phe Pro Tyr Tyr Phe Asp Tyr Trp Gly Gln

Gly Thr Thr Leu Arg Val Ser Ser Val Ser Gly Ser

SEQ ID NO: 2:
Met Gly Phe Lys Met Glu Ser Gln Ile Gln Val Phe Val Tyr Met Leu

Leu Trp Leu Ser Gly Val Asp Gly Asp Ile Val Met Ile Gln Ser Gln

Lys Phe Val Ser Thr Ser Val Gly Asp Arg Val Asn Ile Thr Cys Lys

Ala Ser Gin Asn Val Gly Ser Asn Val Ala Trp Leu Gln Gln Lys Pro

Gly Gin Ser Pro Lys Thr Leu Ile Tyr Ser Ala Ser Tyr Arg Ser Gly

Arg Val Pro Asp Arg Phe Thr Gly Ser Gly Ser Gly Thr Asp Phe Ile

Leu Thr Ile Thr Thr Val Gln Ser Glu Asp Leu Ala Glu Tyr Phe Cys

Gln Gin Phe Asn Arg Ser Pro Leu Thr Phe Gly Ser Gly Thr Lys Leu

Glu Leu Lys Arg Ala Asp Ala Ala Pro Thr Val Ser Ile Phe Pro Pro

Ser Ser Lys Gly Glu Phe

Alternative exemplary antibodies that can be used in the present invention are antibodies comprising an amino acid sequence of a heavy chain variable region as depicted in SEQ ID NO:3 or an amino acid sequence of a light chain variable region as depicted in SEQ ID NO:4. Other exemplary antibodies include antibodies which are derived from antibodies comprising a heavy chain variable region as depicted in SEQ ID NO:3 or an amino acid sequence of a light chain variable region as depicted in SEQ ID NO:4. Yet other exemplary antibodies include antibodies which have the same specificity and/or bind to the same epitope as antibodies comprising a heavy chain variable region as depicted in SEQ ID NO:3 or an amino acid sequence of a light chain variable region as depicted in SEQ ID NO:4. Yet other exemplary antibodies include antibodies which comprise a heavy chain variable region which is at least 70%, at least 80%, at least 90% or at least 95% homologous to the sequence depicted in SEQ ID NO:3. Yet other exemplary antibodies include antibodies which comprise a light chain variable region which is at least 70%, at least 80%, at least 90% or at least 95% homologous to the sequence depicted in SEQ ID NO:4.

SEQ ID NO. 3: heavy MOR
QVQLVESGGGLVQPGGSLRLSCAASGFTFSSYWMNWVRQAPGKGLEWV

SGIENKYAGGATYYAASVKGRFTISRDNSKNTLYLQMNSLRAEDTAVY

YCARGFGTDFWGQGTLVTVSS

SEQ ID NO. 4: light MOR
DIELTQPPSVSVAPGQTARISCSGDSIGKKYAYWYQQKPGQAPVLVIY

KKRPSGIPERFSGSNSGNTATLTISGTQAEDEADYYCSAWDKGMVFG

GGTKLTVLGQ

Alternative exemplary antibodies that can be used in the present invention are antibodies comprising a H-CDR3 sequence selected from:

```
                                       (SEQ ID NO. 5)
   Ser Gly Leu Ile Phe Asp Tyr Trp Leu Asp,
   1               5                   10
```

```
                                       (SEQ ID NO: 6)
   Ser Gly Leu Ile Ile Asp Ala Leu Ser Pro,
   1               5                   10
```

```
                                       (SEQ ID NO: 7)
   Thr Ser Leu Met Ser Ile Tyr Phe Asp Tyr,
   1               5                   10
```

```
                                       (SEQ ID NO: 8)
   Ser Gly Leu Leu Phe Leu Tyr Phe Asp Tyr,
   1               5                   10
```

```
                                       (SEQ ID NO: 9)
   Ser Gly Leu Ile Asn Leu Gly Met His Pro,
   1               5                   10
```

```
                                       (SEQ ID NO: 10)
   Ser Gly Leu Ile Phe Asp Ala Leu Arg Asp,
   1               5                   10
```

```
                                       (SEQ ID NO: 11)
   Ser Gly Leu Ile Phe Asp Lys Leu Thr Ser,
   1               5                   10
```

```
                                       (SEQ ID NO: 12)
   Ser Gly Leu Ile Asn Leu His Phe Asp Thr,
   1               5                   10
```

```
                                       (SEQ ID NO: 13)
   Ser Thr His Phe Ser Ala Tyr Phe Asp Tyr,
   1               5                   10
```

```
                                       (SEQ ID NO: 14)
   Ser Gly Leu Ile Met Asp Lys Leu Asp Asn,
   1               5                   10
```

```
                                       (SEQ ID NO: 15)
   Ser Gly Leu Ile Ile Asp Asn Leu Asn Pro,
   1               5                   10
and
```

```
                                       (SEQ ID NO: 16)
   Ser Gly Leu Ile Ala Val Tyr Phe Asp Tyr.
   1               5                   10
```

Preferably, the antibodies comprising a H-CDR3 sequence selected from any one of SEQ ID NOs. 5-16, additionally comprise the following H-CDR1 sequence:

```
                                 (SEQ ID NO: 17)
    Asp Tyr Leu Leu His,
    1               5
``` and/or the following H-CDR2 sequence:

```
                                              (SEQ ID NO: 18)
Trp Leu Asn Pro Tyr Ser Gly Asp Thr Asn Tyr Ala Gln Lys Phe Gln,
1               5                   10                  15

Gly
``` and/or the following L-CDR1 sequence:

```
                                      (SEQ ID NO: 19)
    Arg Ala Ser Gln Asn Ile Arg Asn Ile Leu Asn,
    1               5                   10
``` and/or the following L-CDR2 sequence:

```
Ala Ala Ser Asn Leu Gln Ser,    (SEQ ID NO: 20)
1               5
``` and/or the following L-CDR3 sequence:

```
                                  (SEQ ID NO: 21)
    Gln Gln Ser Tyr Ser Met Pro Arg Thr.
    1               5
```

Alternative exemplary antibodies that can be used in the present invention are antibodies comprising the following L-CDR1 sequence:

```
                                           (SEQ ID NO: 22)
Arg Ala Ser His Arg Val Ser Ser Asn Tyr Leu Ala,
1               5                   10
``` and/or the following L-CDR2 sequence:

```
Gly Ala Ser Asn Arg Ala Thr,     (SEQ ID NO: 23)
1               5
``` and/or the following L-CDR3 sequence:

```
Gln Gln Tyr Ala Ser Ser Pro Val Thr,  (SEQ ID NO: 24)
1               5
``` and/or the following H-CDR1 sequence:

```
                                        (SEQ ID NO: 25)
    Gly Tyr Ile Phe Pro Thr Phe Ala Leu His,
    1               5                   10
``` and/or the following H-CDR2 sequence:

```
                                                    (SEQ ID NO: 26)
Ser Ile Asn Thr Ala Ser Gly Lys Thr Lys Phe Ser Thr Lys Phe Gln,
1               5                   10                  15
``` and/or the following H-CDR3 sequence:

```
                                              (SEQ ID NO: 27)
Asp Arg Phe Gln Asn Ile Met Ala Th-
r Ile Leu Asp Val.
1               5                   10
```

Preferably said antibody comprise all the CRDs of SEQ ID NOs. 22-27.

The GM-CSF receptor is a member of the haematopoietin receptor superfamily. It is heterodimeric, consisting of an alpha and a beta subunit. The alpha subunit is highly specific for GM-CSF whereas the beta subunit is shared with other cytokine receptors, including IL3 and IL5. This is reflected in a broader tissue distribution of the beta receptor subunit. The alpha subunit, GM-CSFR α, is primarily expressed on myeloid cells and non-haematopoetic cells, such as neutrophils, macrophages, eosinophils, dendritic cells, endothelial cells and respiratory epithelial cells. Full length GM-CSFR α is a 400 amino acid type I membrane glycoprotein that belongs to the type I cytokine receptor family, and consists of a 22 amino acid signal peptide (positions 1-22), a 298 amino acid extracellular domain (positions 23-320), a transmembrane domain from positions 321-345 and a short 55 amino acid intra-cellular domain. The signal peptide is cleaved to provide the mature form of GM-CSFR α as a 378 amino acid protein. cDNA clones of the human and murine GM-CSFR α are available and, at the protein level, the receptor subunits have 36% identity. GM-CSF is able to bind with relatively low affinity to the α subunit alone (Kd 1-5 nM) but not at all to the β subunit alone. However, the presence of both α and β subunits results in a high affinity ligand-receptor complex (Kd>>100 pM). GM-CSF signalling occurs through its initial binding to the GM-CSFR α chain and then cross-linking with a larger subunit the common β chain to generate the high affinity interaction, which phosphorylates the JAK-STAT pathway.

Any antibody specific for GM-CSF receptor may be used with the present invention. Exemplary antibodies include antibodies comprising an amino acid sequence of a H-CDR3 sequence depicted in any one of SEQ ID No's.:28-46. Other exemplary antibodies include antibodies which are derived from antibodies comprising an amino acid sequence of a H-CDR3 sequence depicted in any one of SEQ ID No's.:28-46. Yet other exemplary antibodies include antibodies which have the same specificity and/or bind to the same epitope as antibodies comprising an amino acid sequence of a H-CDR3 sequence depicted in any one of SEQ ID No's.:28-46. Yet other exemplary antibodies include antibodies which comprise a H-CDR3 sequence which is at least 70%, at least 80%, at least 90% or at least 95% homologous to the H-CDR3 sequence depicted in any one of SEQ ID No's.:28-46.

SEQ ID No: 28:
Val Gly Ser Phe Ser Gly Ile Ala Tyr Arg Pro
                5                   10

SEQ ID No: 29:
Val Gly Ser Phe Ser Gly Pro Ala Leu Arg Pro
                5                   10

SEQ ID No: 30:
Val Gly Ser Phe Ser Pro Pro Thr Tyr Gly Tyr
                5                   10

SEQ ID No: 31:
Val Gly Ser Phe Ser Gly Tyr Pro Tyr Arg Pro
                5                   10

SEQ ID No: 32:
Val Gly Ser Phe Ser Pro Leu Thr Leu Gly Leu
                5                   10

SEQ ID No: 33:
Val Gly Ser Phe Ser Gly Pro Val Tyr Gly Leu
                5                   10

SEQ ID No: 34:
Val Gly Ser Phe Ser Pro Pro Ala Tyr Arg Pro
                5                   10

SEQ ID No: 35:
Val Gly Ser Phe Ser Pro Val Thr Tyr Gly Leu
                5                   10

SEQ ID No: 36:
Val Gly Ser Phe Ser Gly Leu Ala Tyr Arg Pro
                5                   10

SEQ ID No: 37:
Val Gly Ser Phe Ser Pro Ile Thr Tyr Gly Leu
                5                   10

SEQ ID No: 38:
Val Gly Ser Phe Ser Gly Trp Ala Phe Asp Tyr
                5                   10

SEQ ID No: 39:
Val Gly Ser Phe Ser Gly Trp Ala Phe Asp Tyr
                5                   10

SEQ ID No: 40:
Leu Gly Ser Val Thr Ala Trp Ala Phe Asp Tyr
                5                   10

SEQ ID No: 41:
Ala Gly Ser Ile Pro Gly Trp Ala Phe Asp Tyr
                5                   10

SEQ ID No: 42:
Val Gly Ser Phe Ser Pro Leu Thr Met Gly Leu
                5                   10

SEQ ID No: 43:
Val Gly Ser Phe Ser Pro Leu Thr Met Gly Leu
                5                   10

SEQ ID No: 44:
Val Gly Ser Phe Ser Gly Pro Ala Leu His Leu
                5                   10

SEQ ID No: 45:
Val Gly Ser Val Ser Arg Ile Thr Tyr Gly Phe
                5                   10

SEQ ID No: 46:
Val Gly Ser Phe Ser Pro Leu Thr Leu Gly Leu
                5                   10

In certain aspects, the present invention provides methods for the treatment of osteoarthritis in a subject, said method comprising the step of administering a GM-CSF antagonist to said subject. "Subject", as used in this context refers to any mammal, including rodents, such as mouse or rat, and primates, such as cynomolgus monkey (*Macaca fascicularis*), rhesus monkey (*Macaca mulatta*) or humans (*Homo sapienss*). Preferably the subject is a primate, most preferably a human.

In certain aspect, the present invention provides a composition comprising a GM-CSF antagonist capable of antagonizing the ability of GM-CSF from activating, proliferating, inducing growth and/or survival of cells in a subject suffering from osteoarthritis, or being suspected of suffering from osteoarthritis, said composition further comprising one or more pharmaceutically acceptable carriers and/or diluents. Anti-GM-CSF antibodies of the present invention may antagonize any of the roles of GM-CSF in osteoarthritis.

In another aspect, the present invention provides a method for the prophylaxis of osteoarthritis in a subject, said method comprising administering a GM-CSF antagonist to said subject. "Prophylaxis" as used in this context refers to methods which aim to prevent the onset of a disease or which delay the onset of a disease.

In certain aspects, the present invention provides a composition comprising a GM-CSF antagonist useful in the treatment of osteoarthritis, said composition further comprising one or more pharmaceutically acceptable carriers and/or diluents.

In other aspects, the present invention provides the use of a GM-CSF antagonist in the preparation of a medicament in the treatment of osteoarthritis.

In other aspects, the present invention provides GM-CSF antagonists for the treatment of osteoarthritis.

The compositions of the present invention are preferably pharmaceutical compositions comprising a GM-CSF antagonist and a pharmaceutically acceptable carrier, diluent or excipient, for the treatment of osteoarthritis. Such carriers, diluents and excipients are well known in the art, and the skilled artisan will find a formulation and a route of administration best suited to treat a subject with the GM-CSF antagonists of the present invention.

In another aspect the present invention provides a genetically engineered mammal having a GM-CSF –/– genotype. In particular aspects said mammal is a mouse. The terms "knock-out" mouse (or mammal), a mouse (or mammal) "disrupted in" a certain gene, and a mouse (or mammal) with a "–/– genotype" are used interchangeably in the present invention and are art recognized. Respective animals are deficient in a respective gene, here GM-CSF, on both alleles of the chromosome.

EXAMPLE 1

Generation of a GM-CSF–/– Mouse

The generation of GM-CSF–/– mice is described in Stanley et al (1994). Proc. Natl. Acad. Sci. USA 91:5592. Briefly, chimeric mice were generated by microinjection of 129/OLA-derived ES cells (H-2b) with a disrupted GM-CSF gene into C57BL/6 (H-2b) host blastocysts. Germline transmitters of the mutated GM-CSF allele were crossed with C57BL/6 mice for 11 generations, giving GM-CSF+/– mice that were interbred to yield the GM-CSF–/–, GM-CSF+/–, and GM-CSF+/+ mice used for the experiments. GM-CSF genotype status was determined by PCR analysis of tail DNA. Animals were fed standard rodent chow and water ad libitum and were housed with same sex littermates in sawdust-lined cages. Mice of both sexes were consigned to experiments at 8 to 15 wk of age

EXAMPLE 2

Validation of GM-CSF as a Target for Osteoarthritis

GM-CSF−/− mice were compared to C57/BL6 mice (see e.g. Mills et al, J Immunol 164:6166-6173, 2000) in an experimental model of osteoarthritis.

Method: Mice (n=10 per group) received an intra-articular injection of collagenase in the left knee on day −2 and day 0 (Blom et al, Arthritis Rheum 56:147-157, 2007). At day 42 the mice were killed, the knee joints collected, fixed, de-calcified, embedded in paraffin and cut at 7 μm with a microtome. Slides were then stained with Safranin-O/Fast Green and Haematoxylin and Eosin to demonstrate joint pathology. Pathology investigated includes: cartilage damage, synovitis, osteophyte formation and joint deformation.

The scoring system used for cartilage pathology was as follows:
Grade
0 Normal
1 Irregular but intact
1.5 Irregular with rough surface
2 Superficial fibrillation
2.5 Superficial fibrillation with reduced cells in cartilage layer
3 Vertical fissures
3.5 Branching and/or horizontal fissures, tidemark ruptures
4 Cartilage loss not extending to the tide mark
4.5 Cartilage loss extending to the tide mark
5 Cartilage loss beyond the tide mark but not extending to the bone
5.5 Cartilage loss extending to the bone
6 Bone loss/remodeling/deformation
Stage
1 <10% area damaged
2 10-25% area damaged
3 25-50% area damaged
4 50-75% area damaged
The grade was multiplied by the stage to give the score.

This scoring system is based on a recognized method to assess OA histopathology in clinical and experimental OA. See Pritzker et al, *Osteoarthritis Cartilage* 14:13-29, 2006. Grade is defined as OA depth progression into cartilage. Stage is defined as the horizontal extent of cartilage involvement, i.e. how much of the cartilage is affected. Grade is multiplied by the stage to give the score to give an overall score, so as to represent a combined assessment of OA severity and extent. Up to six sections are scored per mouse.

Results: Inspection of these joints showed that the GM-CSF−/− mice show less knee joint pathology than the control mice, indicating the role of GM-CSF in normal osteoarthritis pathology and progression. Pathology observed in the C57/Bl6 mice includes severe damage to the cartilage layer, osteophyte formation, joint deformation and synovitis. The GM-CSF−/− mice showed no osteophyte formation or joint deformation and much less cartilage damage and synovitis.

Figure 2:
FIG. 2 shows exemplary histology sections of healthy control knees. Magnification is 100×. No cartilage damage, osteophyte formation, synovitis or deformations can be seen. S=synovial lining, C=cartilage layer.
Figure 3:
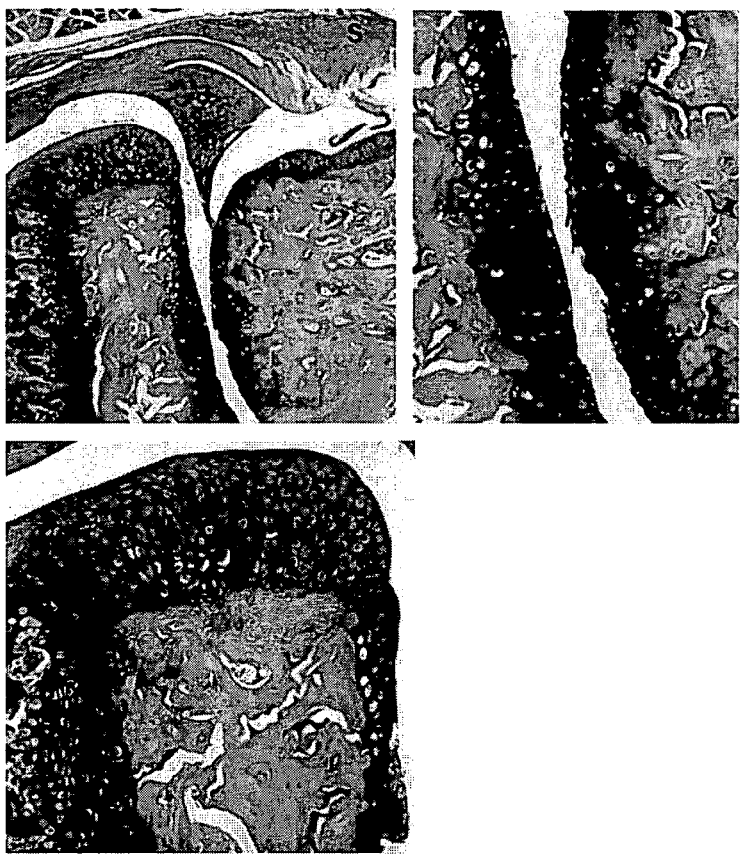
FIG. 3 shows exemplary histology sections of the left knees of C57/BL6 mice in a model of collagenase-induced OA. Magnification is of the individual sections is indicated in the Figures. The top row of pictures shows that cartilage damage, osteophyte formation and synovitis are evident. O=osteophyte. S=synovial lining. The bottom row of pictures shows that joint deformation is also present.
Figure 3:
Figure 4:
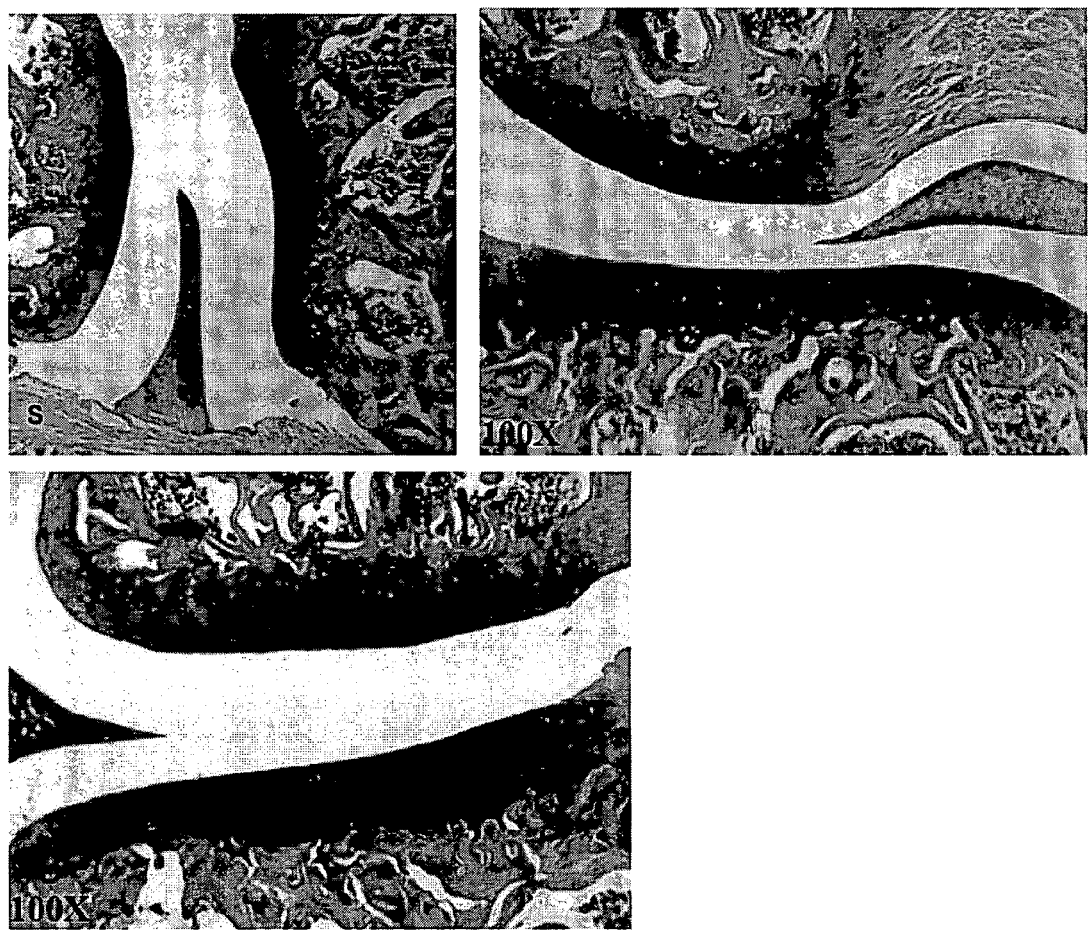
FIG. 4 shows exemplary histology sections of the left knees of GM-CSF-/- mice in a model of collagenase-induced OA. Magnification is of the individual sections is indicated in the Figures. As can be seen, the abnormalities and/or damages are much less severe compared to the C57/BL6 mice (see FIG. 3) and are comparably to the healthy control mice (see FIG. 2). O=osteophyte. S=synovial lining.

Quantitatve data on—joint damage in different regions are shown in FIG. 1. Representative histology is shown in FIGS. 2 (healthy control knees), 3 (C57/BL6 left knees) and 4 (GM-CSF−/− left knees). GM-CSF gene-deficient mice developed less collagenase-induced OA pathology, compared to C57BL/6 mice.

In summary, GM-CSF−/− mice showed strongly decreased knee joint pathology compared to C57/BL6 mice in an experimental model of osteoarthritis and validated GM-CSF as a drug target for therapeutic intervention for osteoarthritis.

EXAMPLE 3

Therapeutic Effectiveness of GM-CSF Antagonists in the Treatment of OA

In this experiment we used a monoclonal antibody specific for GM-CSF to demonstrate that a GM-CSF antagonist can be effective to treat osteoarthritis.
Collagen-induced OA mouse model:
C57BL/6 mice were given 1 unit of collagenase type VII intra-articularly into the right knee on days 0 and 2 to induce joint instability (see Blom et al. (2004) Osteoarthritis Cartilage. 12; 627-35).
Anti-GM-CSF antibody treatment:
20 mice were randomly divided into 2 groups (10 mice/group).
Group 1 (n=10): anti-GM-CSF antibody (22E9)
Group 2 (n=10): IgG2a isotype control antibody.
Mice were treated intraperitoneally, three times per week for 6 weeks with 250 μg/mouse/treatment anti-GM-CSF antibody (22E9) or IgG2a isotype control antibody. Treatment started 4 days before the induction of OA (prophylactic), i.e. mice were treated on day −4, day −2, day 0 (the day of the first collagenase injection), then 3 times per week until the end of the experiment at 6 weeks). At weeks 2, 4 and 6, mice were bled. Serum will be checked for antibody content and immunogenicity against 22E9. Both, the control antibody and the anti-GM-CSF antibody were purified to contain less than 10 Endotoxin Units/ml.

The antibody 22E9 was used as an exemplary anti-GM-CSF antibody. 22E9, which is of IgG2a isotype, is a rat anti-mouse GM-CSF-specific antibody. 22E9 was purchased from AbD Serotec (Martinsried, Germany; Cat. No. 1023501). Alternative suppliers exist, e.g. eBioscience (San Diego, Calif., USA, Cat. No. 14-7331).
Histology:
6-weeks post final injections, histology was performed on the mice knee joints. The knee joints were collected, fixed, de-calcified, embedded in paraffin and cut at 7 μm with a microtome. Slides were stained with Safranin-O/Fast Green and Haematoxylin and Eosin to demonstrate joint pathology. Pathology investigated included: cartilage damage, synovitis, osteophyte formation and joint deformation.

The same scoring system as in Example 2 was used for cartilage pathology. Grade was multiplied by the stage to give the score.

Figure 5:
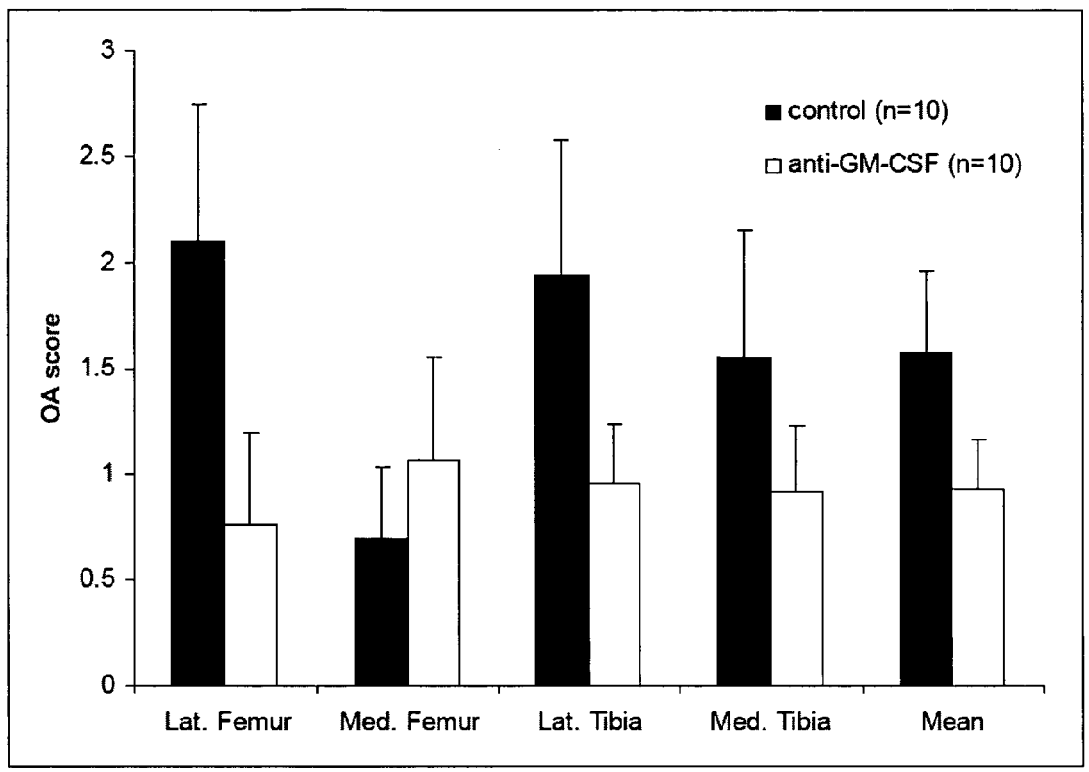
FIG. 5 shows the knee joint histology scoring of the therapeutic treatment with a GM-CSF antibody in a mouse model of OA. Lat.=Lateral. Med.=Medial. Results are expressed as mean±SEM. As can be seen mice treated with anti-GM-CSF antibody show less disease.

The following scoring system was used for synovitis (Synovial layer scoring system):
0 No changes compared to normal joints
1 Thickening of the synovial lining and some influx of inflammatory cells
2 Thickening of the synovial lining and intermediate influx of inflammatory cells
3 Profound thickening of the synovial lining and maximal observed influx of inflammatory cells
Pain measurements:
An indicator of pain used for OA models is differential distribution of weight measured using an Incapacitance Meter. This instrument measures changes in weight distribution between the operated and contralateral, unoperated hind limb. Mice were allowed to acclimatize to the equipment on three occasions prior to the experiment. Weight placed on each hind limb was measured over a 5 second period. Three separate measurements taken per mouse for each time point then averaged. Measurements were performed 2 times per week throughout the experiment. Results are expressed as collagenase injected limb/control limb×100.
Results:
For all areas analyzed in histology (except the Medial Femur), i.e. the Lateral Femur, the Lateral Tibia, and the Medial Tibia, there was a clear trend towards less disease in mice treated with anti-GM-CSF antibody. Results are depicted in FIG. 5.

Figure 6:
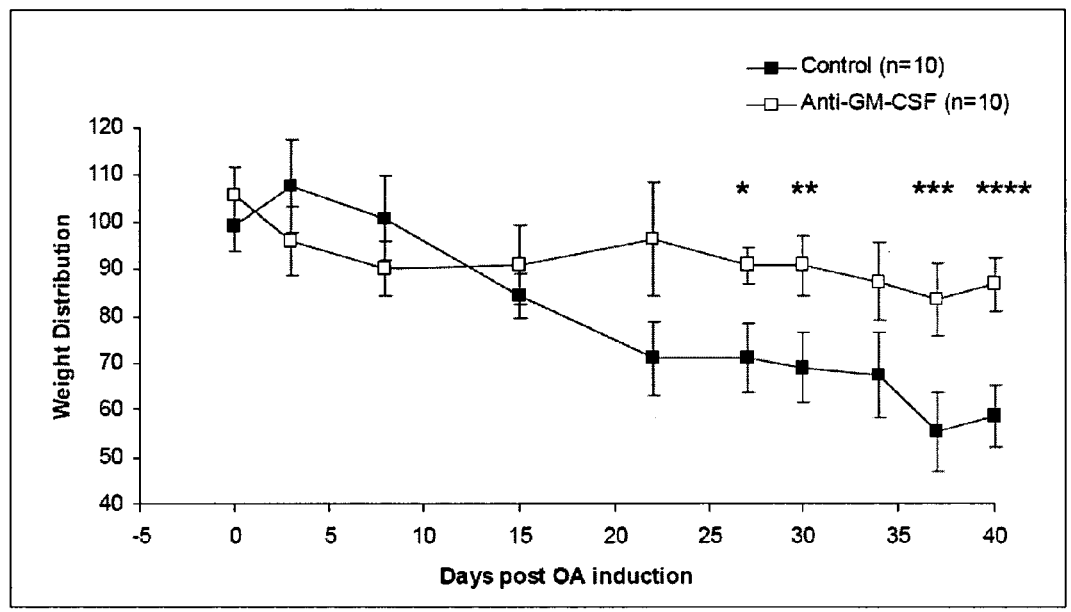
FIG. 6 shows the result of an experiment assessing the hind limb weight distribution in an incapacitance meter. Data are significant (unpaired t-test) from day 27 post OA induction onwards, as indicated in the graph.

Assessment of the weight distribution, as a measure of pain associated with the arthritis, showed a significant shift in weight away from the arthritic knee from day 27 onwards in the anti-GM-CSF mAb-treated group compared to the control mAb-treated group. Results are depicted in FIG. 6.

Mice treated with a GM-CSF antagonist showed less disease as compared to mice treated with the control antibody. Mice treated with the GM-CSF antagonist also showed significantly less pain in the latter stages of disease compared to mice treated with the control antibody. Mice treated with the isotype control antibody showed significant increased signs of osteoarthritis as compared to the mice which received the GM-CSF-specific antibody. This demonstrates that GM-CSF antagonists are effective in the treatment of OA.

EXAMPLE 4

Therapeutic Effectiveness of a GM-CSF Specific Antibody Comprising SEQ ID Nos. 1 or 2

Example 3 is repeated, whereby as GM-CSF antagonist, a GM-CSF specific antibody comprising an amino acid sequence of a heavy chain variable region as depicted in SEQ ID NO:1 or comprising an amino acid sequence of a light chain variable region as depicted in SEQ ID NO:2 is used. Another species than mouse may be used, in particular a species to which the antibody used in this experiment is cross reactive. Preferably the animal species used in this experiment is rat.

The animals treated with the isotype control antibody shows significant increased signs of osteoarthritis as compared to the animals which received a GM-CSF specific antibody comprising an amino acid sequence of a heavy chain variable region as depicted in SEQ ID NO:1 or comprising an amino acid sequence of a light chain variable region as depicted in SEQ ID NO:2. This demonstrates the effectiveness of the antibodies in the treatment of OA.

EXAMPLE 5

Therapeutic Effectiveness of a GM-CSF Specific Antibody Comprising SEQ ID NOs. 3 or 4

Example 3 is repeated. As GM-CSF antagonist, a GM-CSF specific antibody comprising an amino acid sequence of a heavy chain variable region as depicted in SEQ ID NO:3 or comprising an amino acid sequence of a light chain variable region as depicted in SEQ ID NO:4 is used. Another species than mouse may be used, in particular a species to which the antibody used in this experiment is cross reactive. Preferably the animal species used in this experiment is rat.

The animals, e.g. rat, treated with the isotype control antibody show significant increased signs of osteoarthritis as compared to the animals which received a GM-CSF specific antibody comprising an amino acid sequence of a heavy chain variable region as depicted in SEQ ID NO:3 or comprising an amino acid sequence of a light chain variable region as depicted in SEQ ID NO:4. This demonstrates the effectiveness of the antibodies in the treatment of OA.

EXAMPLE 6

Therapeutic Effectiveness of a GM-CSF Specific Antibodies Comprising SEQ ID NOs. 5-20

Example 3 is repeated. As GM-CSF antagonist, a GM-CSF specific antibody comprising a H-CDR3 sequence selected from any one of SEQ ID NOs. 5-16 is used. Preferably, said antibodies additionally comprise the H-CDR1 sequence of SEQ ID NO:16, and/or the H-CDR2 sequence of SEQ ID NO:17, and/or the L-CDR1 sequence of SEQ ID NO:18, and/or the L-CDR2 sequence of SEQ ID NO:19), and/or the L-CDR3 sequence of SEQ ID NO:20. Another species than mouse may be used, in particular a species to which the antibody used in this experiment is cross reactive. Preferably the animal species used in this experiment is rat.

The animals, e.g. rat, treated with the isotype control antibody show significant increased signs of osteoarthritis as compared to the animals which received a GM-CSF specific antibody according to the present example. This demonstrates the effectiveness of the antibodies in the treatment of OA.

EXAMPLE 7

Therapeutic Effectiveness of a GM-CSF Specific Antibodies Comprising SEQ ID NOs. 21-26

Example 3 is repeated. As GM-CSF antagonist, a GM-CSF specific antibody comprising the L-CDR1 sequence of SEQ ID NO:22, and/or the L-CDR2 sequence of SEQ ID NO:23, and/or the L-CDR3 sequence of SEQ ID NO:24, and/or the H-CDR1 sequence of SEQ ID NO:25, and/or the H-CDR2 sequence of SEQ ID NO:26, and/or the H-CDR3 sequence of SEQ ID NO:27 is used. Preferably said antibody comprise all the CRDs of SEQ ID NOs. 22-27. Another species than mouse may be used, in particular a species to which the antibody used in this experiment is cross reactive. Preferably the animal species used in this experiment is rat.

The animals, e.g. rat, treated with the isotype control antibody show significant increased signs of osteoarthritis as compared to the animals which received a GM-CSF specific antibody according to the present example. This demonstrates the effectiveness of the antibodies in the treatment of OA.

EXAMPLE 8

Therapeutic Effectiveness of Antibodies Specific for the GM-CSF Receptor

Example 3 is repeated with the difference that a monoclonal antibody specific for the GM-CSF receptor is used instead of a monoclonal antibody specific for the GM-CSF.

As GM-CSF antagonist, a GM-CSF receptor specific antibody comprising an amino acid sequence of a H-CDR3 sequence depicted in any one of SEQ ID No's.:27-45 is used. Another species than mouse may be used, in particular a species to which the antibody used in this experiment is cross reactive. Preferably the animal species used in this experiment is rat.

The animals, e.g. rat, treated with the isotype control antibody show significant increased signs of osteoarthritis as compared to the animals which received a GM-CSF receptor specific antibody according to the present example. This demonstrates the effectiveness of the antibodies in the treatment of OA.

EXAMPLE 9

Clinical Trial

A clinical trial is performed in adult patients suffering from osteoarthritis of the knee The objective of the randomized, double-blind, placebo-controlled clinical trial is to determine the comparative differences between the GM-CSF antagonists of the present invention and placebo in overall pain relief and quality of life in a total sample of 30 patients with diagnosed osteoarthritis (OA) of the knee. Another objective is to determine the safety and tolerability of the GM-CSF antagonists of the present invention as determined by the adverse events, physical examination and vital signs.
Methods:

Thirty patients (about 15 adult males and 15 adult females), aged 40 and over, with a clinical diagnosis of osteoarthritis of the knee(s) and verified knee pain for at least 15 days in the month prior to testing are enrolled in the study. Patients receive a therapeutically effective amount of GM-CSF antagonists or a placebo (e.g. once every two weeks for about six months).

The Western Ontario and McMaster Universities Osteoarthritis Index (WOMAC; Bellamy et al, *J Rheumatol* 15(12): 1833-40, 1988) and the SF-36v2 Quality of Life instrument scales (Quality Metric Health Outcomes Solutions, Lincoln, R.I.) are used in the study. The WOMAC is a disease-specific, self-administered, health status measure. It probes clinically-important symptoms in the areas of pain, stiffness and physical function in patients with osteoarthritis of the hip and/or knee. The index consists of 24 questions (5—pain, 2—stiffness and 17—physical function) and can be completed in less than 5 minutes. The WOMAC is a valid, reliable and sensitive instrument for the detection of clinically important changes in health status following a variety of interventions (pharmacologic, nutritional, surgical, physiotherapy, etc.). The WOMAC questionnaire is valid for assessing the effects of intervention on hip or knee osteoarthritis. The SF-36v2 Quality of Life instrument is a multi-purpose, short-form health survey with 36 questions. It yields an 8-scale profile of functional health and well-being scores as well as psychometrically-based physical and mental health summary measures and a preference-based health utility index. It is a generic measure, as opposed to one that targets a specific age, disease, or treatment group. Accordingly, the SF-36v2 has proven useful in surveys of general and specific populations, comparing the relative burden of diseases, and in differentiating the health benefits produced by a wide range of different treatments. The SF-36v2 yields information on the following aspects and subsets of health; Physical Health (comprised of physical functioning, role-physical, bodily pain and general health) and Mental Health (comprised of vitality, social functioning, role—emotional and mental health).
Results:

Change in bodily pain: The improvement in SF-36v2 bodily pain is statistically significant in patients treated with the GM-CSF antagonists of the present invention as compared with placebo. A higher score is better because it means the patient feels less pain after taking the product. There is a statistical significant improvement in the bodily-pain score in the group that received the GM-CSF antagonists of the present invention versus the placebo group.

Change in role-physical score: The superior effect of the GM-CSF antagonists of the present invention compared with the placebo is statistically significant in week 8, week 12, and week 20 in terms of role limitations due to physical health (role physical). A higher score is better because it means that the patient noticed a physical improvement and a reduction in the limitations suffered in activities of daily living. There is a statistical significant improvement in the role-physical score in the group that received the GM-CSF antagonists of the present invention versus the placebo group.

Change in the total WOMAC score: The total WOMAC score of the group treated with the GM-CSF antagonists of the present invention is statistical significantly better than the total WOMAC score of the placebo group (a lower score is better).

Change in WOMAC ADL: The improvement in activities of daily living (measured as a WOMAC ADL sub-score) is greater in the group treated with the GM-CSF antagonists of the present invention than in the placebo group. There is an statistically significant improvement in the WOMAC ADL score in the group treated with the GM-CSF antagonists of the present invention compared to the placebo group (a lower score is better).
Conclusions:

The clinical trial shows the efficacy of the GM-CSF antagonists of the present invention in improving the quality of life of patients with osteoarthritis of the knee. The results of the clinical trial also show the product's safety and tolerance, given that no serious adverse effects were found.

The efficacy of the GM-CSF antagonists of the present invention can also be established through studies in other species to which the GM-CSF antagonists of the present invention are cross-reactive (e.g. on horses in order to evaluate joint movement); and by using in vitro studies to determine the ability of GM-CSF antagonists of the present invention to inhibit IL-1-induced agrecan degradation, conducting the assay on condrocyte cultures.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.
Bibliography
Bellamy et al, *J Rheumatol* 15(12):1833-40, 1988
Blom et al, *Arthritis Rheum* 56:147-157, 2007
Ghose et al, *J Combin Chem:* 1:55-68, 1999
Knappik et al, *J. Mol. Biol.* 296:57, 2000
Krebs et al, *J. Immunol. Methods.* 254:67, 2001
Lipinski et al, *Adv Drug Del Rev* 23:3-25, 1997
Mills et al, *J Immunol* 164:6166-6173, 2000
Pritzker et al, *Osteoarthritis Cartilage* 14:13-29, 2006
Rothe et al, *J. Mol. Biol.* 376:1182, 2008

The invention claimed is:

1. A method for the treatment of osteoarthritis in a human subject, comprising the step administering to the subject an effective amount of an antibody specific for GM-CSF, wherein the antibody specific for GM-CSF comprises the heavy chain variable region amino acid sequence of SEQ ID NO: 3 and the light chain variable region amino acid sequence of SEQ ID NO: 4.

* * * * *